United States Patent [19]

Najer et al.

[11] 4,267,328

[45] May 12, 1981

[54] 1-PHENYLPIPERAZINES

[75] Inventors: Henry Najer, Paris; Philippe Manoury, Le Plessis-Robinson, both of France

[73] Assignee: Synthelabo, Paris, France

[21] Appl. No.: 61,245

[22] Filed: Jul. 27, 1979

[30] Foreign Application Priority Data

Aug. 1, 1978 [FR] France ............................. 78 22672
Nov. 23, 1978 [FR] France ............................. 78 33105
Jun. 22, 1979 [FR] France ............................. 79 16030

[51] Int. Cl.³ .................... C07D 295/06; A01N 43/60
[52] U.S. Cl. .................................. 544/394; 544/392; 424/250
[58] Field of Search ............................. 544/394, 395

[56] References Cited

U.S. PATENT DOCUMENTS

| | | | |
|---|---|---|---|
| 2,836,594 | 5/1958 | Parcell | 544/394 |
| 3,007,928 | 11/1961 | Parcell | 544/394 |
| 3,028,390 | 4/1962 | Parcell | 544/394 |
| 3,170,926 | 2/1965 | Ash et al. | 544/394 |
| 3,929,792 | 12/1975 | Bouchara | 544/394 |
| 3,954,763 | 5/1976 | Giudicelli et al. | 544/394 |

*Primary Examiner*—Anton H. Sutto
*Attorney, Agent, or Firm*—Wegner & Bretschneider

[57] ABSTRACT

Phenylpiperazine derivatives having the general formula (I)

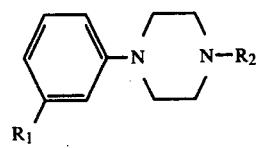

(I)

in which $R_1$ represents a radical $S(O)_m R_3$, $S(O)_n CF_3$ or

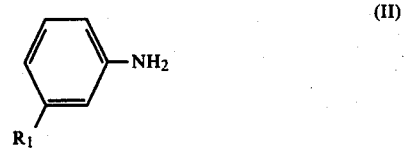

in which radicals m is 0, 1 or 2, n is 1 or 2, $R_3$ is an alkyl radical having 1 to 10 carbon atoms and $R_4$ and $R_5$ independently represent a hydrogen atom or an alkyl radical having 1 to 4 carbon atoms, or the N atom, $R_4$ and $R_5$ together form a heterocyclic ring, which can contain another hetero-atom, and $R_2$ represents a hydrogen atom, the radical $CH_2$—$CH_2$—OH or a radical of formula $CH_2$—$CH_2$—O—$COR_6$, $CH_2$—$CH_2$—O—$CONHR_6$ or $CH_2$—$CH_2$—O—$R_6$ in which radicals $R_6$ being an alkyl radical having 1 to 6 carbon atoms and their pharmaceutically acceptable acid addition salts are useful psychotropic agents and analgesics. Compounds in which $R_1$ is —$SCH_3$ and simultaneously $R_2$ is H are not part of the invention. These derivatives can be prepared by reacting an aniline derivative of formula

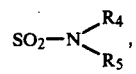

(II)

with a compound of formula

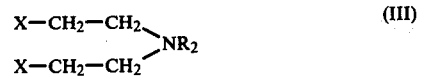

(III)

in which X represents a halogen atom or OH, alkyl—$SO_3$ or aryl—$SO_3$ group or the two X symbols together represent a divalent oxygen atom, thereby completing a morpholine ring.

3 Claims, No Drawings

1-PHENYLPIPERAZINES

DESCRIPTION

The present invention relates to 1-phenylpiperazine derivatives, useful in therapy.

The phenylpiperazine derivatives according to the invention are compounds of the formula (I)

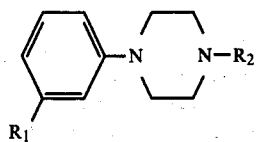

in which $R_1$ represents a radical $S(O)_mR_3$, $S(O)_nCF_3$ or

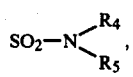

in which radicals m is 0, 1 or 2, n is 1 or 2, $R_3$ is an alkyl radical having 1 to 10 carbon atoms and $R_4$ and $R_5$ independently represent a hydrogen atom or an alkyl radical having 1 to 4 carbon atoms, or N, $R_4$ and $R_5$ together form a heterocyclic ring, which can contain another hetero-atom, and $R_2$ represents a hydrogen atom, the radical $CH_2$—$CH_2$—OH or a radical of formula $CH_2$—$CH_2$—O—$COR_6$, $CH_2$—$CH_2$—O—$CONHR_6$ or $CH_2$—$CH_2$—O—$R_6$, $R_6$ being an alkyl radical having 1 to 6 carbon atoms, with the exception of the compound in which $R_2$ is H when $R_1$ is the radical —$SCH_3$; and the pharmaceutically acceptable acid addition salts of the above compounds of formula (I). Preferably m or n is 1 or 2.

Preferred classes of phenylpiperazine derivatives as defined above are (a) those in which $R_2$ is H, $CH_2CH_2OH$ or $CH_2CH_2OCOCH_3$ and (b) those in which $R_2$ is H or $CH_2CH_2OCOCH_3$ and $R_1$ is $SO_2CF_3$. In class (a) $R_1$ is most preferably $SOCF_3$.

The invention provides a process of preparing the above-defined phenylpiperazine derivatives, which comprises reacting an aniline derivative of formula

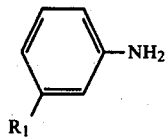

in which $R_1$ is as defined above, with a compound of formula

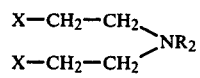

in which X represents a halogen atom or OH, alkyl-$SO_3$, or aryl-$SO_3$ group or the two X symbols together represent a divalent oxygen atom, thereby completing a morpholine ring.

The cyclisation can be carried out in the presence of a solvent, such as an alcohol, or in the absence of solvent. Heating will usually be required.

The compounds (I) in which $R_2$ is other than H can be obtained from the corresponding compound (I) in which $R_2$ is H, by reaction with a compound of formula $R_2Y$ (where Y is a halogen atom or an alkyl-$SO_3$ or aryl-$SO_3$ group).

The compounds (I) in which $R_2$ is $CH_2$—$CH_2$—$OR_6$, $CH_2$—$CH_2$—$OCOR_6$ or $CH_2$—$CH_2$—$OCONHR_6$ can also be prepared from the compound (I), in which $R_2$=$CH_2$—$CH_2$—OH, by reaction with an acid or a functional derivative of an acid (halide or anhydride) or with a halide $R_6$Hal or with an isocyanate.

The compounds (I) in which $R_1$=$S(O)_mR_3$ or $S(O)_nCF_3$ can also be prepared by oxidising the corresponding compounds (I) in which $R_1$=$SR_3$ or $SCF_3$.

The compounds (I) in which $R_2$ is $CH_2CH_2OH$ can be obtained from the corresponding phenylpiperazine compounds (I) in which R is hydrogen by reaction thereof with a compound of formula $XCH_2CH_2OH$ where X is a halogen atom or a mesyl or tosyl group.

The pharmaceutically acceptable acid addition salts of compounds (I) can be prepared from the free bases by a method known per se.

The non-limiting Examples below illustrate the invention.

Temperatures are in °C. The analyses and the IR and NMR spectra confirm the structure of the phenylpiperazine derivatives.

EXAMPLE 1

1-(3-Trifluoromethylsulphonylphenyl)-piperazine and its monohydrochloride.

[$R_1$=$SO_2CF_3$, $R_2$=H]

13.5 g of 3-trifluoromethylsulphonylaniline and 10.7 g of di-(2-chloroethyl)-amine hydrochloride are placed in a 100 ml Erlenmeyer flask equipped with a reflux condenser and a magnetic stirrer. This mixture is heated for 32 hours at 150°. A 30% excess of the halogenoamine hydrochloride is added during the reaction.

When all the starting aniline has reacted, the reaction mixture is taken up in methylene chloride, the resulting mixture is rendered alkaline with N sodium hydroxide solution and the organic solution is decanted, washed with water, dried over sodium sulphate and evaporated to dryness. The desired oily base is thus isolated. It is taken up in toluene and the mixture is decolourised with animal charcoal at the reflux temperature. After hot filtration, the solvent is evaporated off and the base is distilled. The hydrochloride is prepared by reacting the liquid base with hydrochloric acid in ether. The precipitated salt is recrystallized from a mixture of acetone and absolute ethanol. The 1-(3-trifluoromethylsulphonylphenyl)-piperazine hydrochloride melts at 176° C.

EXAMPLE 2

2-[4-(3-Octylsulphonylphenyl)-piperazine-1-yl]-ethanol and its acid fumarate.

[$R_1$=$SO_2$—$CH_2$—$(CH_2)_6$—$CH_3$, $R_2$=$CH_2$—$CH_2$—OH]

6.4 g (0.018 mol) of 1-(3-octylsulphonylphenyl)-piperazine, 2.3 g of sodium carbonate, 2.8 g (1.6 ml=0.022 mol) of glycol bromohydrin, a few crystals of sodium iodide and 150 ml of ethanol are placed in a 250 ml Erlenmeyer flask equipped with a reflux condenser and a magnetic stirrer. (The starting piperazine is prepared in the same manner as in Example 1, the cyclisation being carried out in butanol).

The mixture is heated to the reflux temperature of the ethanol and kept at the boil for 8 hours. After this period, an 80% excess of glycol bromohydrin and sodium carbonate is added.

When all the piperazine has reacted, the ethanol is evaporated off, the residual oil is taken up in a mixture of water and ether and the ether phase is decanted, washed with water, dried over sodium sulphate and concentrated to dryness.

The oily piperazinoethanol derivative is thus isolated.

Its acid fumarate is prepared by reacting fumaric acid with the base in acetone. The salt crystallises slowly on adding a small amount of ether. It is isolated by filtration, dried and recrystallized from acetone. It melts at 113.6° C.

EXAMPLE 3

1-(3-Trifluoromethylsulphinylphenyl)-piperazine and its acid fumarate

[$R_1$=SOCF$_3$; $R_2$=H]

6.27 g (0.03 mol) of 3-trifluoromethylsulphinylaniline and 5.34 g (0.03 mol) of di-(2-chloroethyl)-amine hydrochloride are introduced into a 50 ml Erlenmeyer flask. This mixture is heated to 170° and kept at this temperature for 8 hours. When all the starting aniline has reacted, the reaction mixture is taken up in methylene chloride, the resulting mixture is rendered alkaline with sodium hydroxide, the organic layer is decanted and washed with water and this organic phase is dried over sodium sulphate and evaporated to dryness. The desired base is thus obtained in the form of an oil which is taken up in toluene, and the mixture is decolourised with animal charcoal at the reflux temperature. After filtration, the solvent is evaporated off and the base is distilled.

Its acid fumarate is prepared by reacting the base with fumaric acid in ethanol. The salt is filtered off and recrystallized from ethanol.

The acid fumarate of 1-(3-trifluoromethylsulphinylphenyl)-piperazine melts at 176.2° C.

EXAMPLE 4

2-[4-(3-Trifluoromethylsulphinylphenyl)-piperazino]-ethanol and its acid oxalate.

[$R_1$=SOCF$_3$; $R_2$=CH$_2$—CH$_2$OH]

10 g (0.0359 mol) of 1-(3-trifluoromethylsulphinylphenyl)-piperazine, 4.99 g (2.83 ml or 0.039 mol) of glycol bromohydrin, 4.24 g of sodium carbonate, a few crystals of sodium iodide and 100 ml of ethanol are introduced into a 250 ml Erlenmeyer flask.

The mixture is heated to the reflux temperature and kept at the boil for 6 hours. After evaporation to dryness, the oily residue is taken up in water and ether. The organic phase is decanted, washed with water, dried over sodium sulphate and evaporated to dryness.

The crude oily base is thus obtained.

Its oxalate is prepared by solubilising the base in the minimum amount of absolute ethanol and adding oxalic acid. The precipitated salt is filtered off, dried and recrystallised from ethanol.

The acid oxalate of 2-[4-(3-trifluoromethylsulphinylphenyl)-piperazino]-ethanol melts at 119° C.

EXAMPLE 5

2-[4-(3-Trifluoromethylsulphinylphenyl)-piperazino]-1-acetoxyethane and its acid oxalate

[$R_1$=SOCF$_3$; $R_2$=CH$_2$CH$_2$OCOCH$_3$]

2 g (0.062 mol) of 2-[4-(3-trifluoromethylsulphinylphenyl)-piperazino]-ethanol, 11.42 ml of acetic anhydride and 1 or 2 drops of acetyl chloride, dissolved in 50 ml of anhydrous toluene, are placed in a 100 ml Erlenmeyer flask equipped with a reflux condenser and a magnetic stirrer. The mixture is kept at a temperature of 60° for 1 hour and then evaporated to dryness, the residue is taken up in ether and the organic phase is washed with N sodium hydroxide solution. After decantation, the organic phase is dried over magnesium sulphate and evaporated again.

The resulting ester is an oil which is converted to the acid oxalate in absolute ethanol. By crystallisation from a mixture of ethanol and methanol (80/20), the pure acid oxalate of 2-[4-(3-trifluoromethylsulphinylphenyl)-piperazino]-1-acetoxyethane, which melts at 190° C., is obtained.

EXAMPLE 6

2-[4-(3-Methylthiophenyl)-piperazin-1-yl]-ethanol and its hydrochloride.

[$R_1$=CH$_3$S, $R_2$=CH$_2$CH$_2$OH]

100 ml of ethanol, 10 g (0.048 mol) of 1-(3-methylthiophenyl)-piperazine (prepared in accordance with U.S. Pat. No. 2,976,290), 5.5 g of sodium carbonate, a few crystals of sodium iodide and 3.7 ml of glycol bromohydrin are introduced into a 250 ml ground glass Erlenmeyer flask equipped with a magnetic stirrer and a reflux condenser. The mixture is heated at the reflux temperature for 6 hours and 3.7 ml of glycol bromohydrin and 5.5 g of sodium carbonate are then added. The insoluble material is filtered off after refluxing for 4 hours; the ethanol is evaporated to dryness, the evaporation residue is taken up in water and the mixture is rendered alkaline with sodium hydroxide; extraction is carried out with chloroform; the chloroform extract is washed with water, dried over sodium sulphate and evaporated to dryness. This yields an oil which is converted directly to the hydrochloride.

Preparation of the salt

The base is solubilised in the minimum amount of absolute alcohol, and 9.3 ml of a 4.6 N solution of hydrogen chloride in ether are added dropwise. The hydrochloride precipitates; it is filtered off, drained and dried before being recrystallised from ethanol. The product, which melts at 147° C., is obtained.

The following Table shows the compounds 1 to 10 prepared by way of examples. These compounds in the form of their free bases and all their pharmaceutically acceptable acid addition salts, constitute a specific embodiment of the phenylpiperazine derivatives according to the invention.

TABLE

| Compounds | $R_1$ | $R_2$ | Melting point °C. of an acid addition salt | |
|---|---|---|---|---|
| 1 | $SC_3H_7$—n | $CH_2$—$CH_2$—OH | Monohydrochloride | 114.3 |
| 2 | $SO_2$—$CF_3$ | $CH_2$—$CH_2$—OH | Monohydrochloride | 193.4 |
| 3 (Example 1) | $SO_2$—$CF_3$ | H | Monohydrochloride | 176 |
| 4 | $SO_2$—$CH_2$—$(CH_2)_6$—$CH_3$ | H | Acid fumarate | 161.5 |
| 5 (Example 2) | $SO_2$—$CH_2$—$(CH_2)_6$—$CH_3$ | $CH_2$—$CH_2$—OH | Acid fumarate | 113.6 |
| 6 | $SO_2$—$CH_3$ | $CH_2$—$CH_2$—OH | Monohydrochloride | 247.2 |
| 7 (Example 3) | $SOCF_3$ | H | Acid fumarate | 176.2 |
| 8 (Example 4) | $SOCF_3$ | $CH_2CH_2OH$ | Acid oxalate | 119 |
| 9 (Example 5) | $SOCF_3$ | $CH_2CH_2OCOCH_3$ | Acid oxalate | 190 |
| 10 (Example 6) | $SCH_3$ | $CH_2CH_2OH$ | Hydrochloride | 147 |

The phenylpiperazine derivatives were subjected to pharmacological tests in various fields, in particular in the field of the central nervous system and in the field of analgesics.

The acute toxicity of the compounds was determined by oral administration to mice. The $LD_{50}$ varies from 150 to 700 mg/kg.

The phenylpiperazine derivatives are psychotropic agents. Their activity was measured using the 4-plate test (C. ARON, Thesis in Medicine, Paris 1970, and J. R. BOISSIER, P. SIMON and C. ARON, European J. Pharmacol., 1968, 4, 145–151).

The phenylpiperazine derivatives are administered orally in several doses.

The percentages of disinhibition, measured in mice, varied from 40 to 100% at a dose of 1 mg/kg, from 120 to 200% at a dose of 3 mg/kg and from 140 to 270% at a dose of 10 mg/kg.

The phenylpiperazine derivatives possess psychotropic properties which enable them to be used for the treatment of anxiety and depression.

They can be administered orally, endorectally or parenterally with any suitable excipient and in all the forms of administration corresponding to these methods, namely sugar-coated pills, capsules, cachets, tablets, dragees, solutions or suspensions to be taken orally, suppositories and injectable solutions.

The daily posology can range from 5 to 200 mg.

Furthermore, the phenylpiperazine derivatives were also subjected to pharmacological tests in the field of analgesics, in particular to the test of Koster et al; involving the intraperitoneal injection of acetic acid into mice (Fed. proc. 1959, 18, 42), modified by Peterfalvi, Branceni et al. (Med. Pharmacol. Exp. 1966, 15, 254), in which the 50% active dose for one of the compounds is 7 mg/kg, administered orally, and to the hot-plate test (Eddy and Leimbach) (J. Pharm. Exp. Therap. 1953, 107, 386), in which the 50% active doses are 50 mg/kg after 30 minutes and 100 mg/kg after 60 minutes for one of the compounds chosen by way of example.

These results show that the compounds of the invention possess an essentially peripheral analgesic action. In fact, the $AD_{50}$ in the Koster test is low, whereas the $AD_{50}$ in the hot-plate test is higher.

The compounds can be used for the treatment of various algias, such as headaches, neuralgia, dental pain, rheumatic and traumatic algias and visceral pain.

For this purpose, the compounds of the invention can be presented in any form which is suitable for oral, parenteral or endorectal administration, for example in the form of tablets, sugar-coated pills, injectable solutions, suppositories or the like, with a suitable excipient.

The daily posology can range from 50 mg to 1000 mg.

We claim:

1. A compound of the formula:

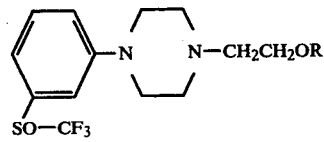

wherein R is hydrogen, alkyl of less than 7 carbon atoms or —CO-alkyl wherein the alkyl group contains less than 7 carbon atoms or pharmaceutically acceptable salts thereof.

2. A compound according to claim 1 which is 2-[4-(3-trifluoromethylsulfinylphenyl)-piperazino]ethanol or pharmaceutically acceptable salts thereof.

3. A compound according to claim 1 which is 2-[4-(3-trifluoromethylsulfinylphenyl)-piperazino]-1-acetoxyethane or pharmaceutically acceptable salts thereof.

* * * * *